(12) United States Patent
Lochan

(10) Patent No.: US 12,310,769 B2
(45) Date of Patent: May 27, 2025

(54) METHOD FOR PERFORMING ANGIOGRAPHY AND ANGIOPLASTY WITHIN LUMEN OF A BLOOD VESSEL

(71) Applicant: Rajeev Lochan, Dubai (AE)

(72) Inventor: Rajeev Lochan, Dubai (AE)

(*) Notice: Subject to any disclaimer, the term of this patent is extended or adjusted under 35 U.S.C. 154(b) by 0 days.

(21) Appl. No.: 17/016,645

(22) Filed: Sep. 10, 2020

(65) Prior Publication Data
US 2022/0296183 A1    Sep. 22, 2022

(51) Int. Cl.
| | |
|---|---|
| *A61B 6/00* | (2024.01) |
| *A61B 6/12* | (2006.01) |
| *A61B 6/50* | (2024.01) |
| *A61F 2/00* | (2006.01) |
| *A61F 2/958* | (2013.01) |
| *A61M 25/00* | (2006.01) |
| *A61M 25/10* | (2013.01) |
| *A61B 8/12* | (2006.01) |

(52) U.S. Cl.
CPC ............. *A61B 6/12* (2013.01); *A61B 6/481* (2013.01); *A61B 6/504* (2013.01); *A61F 2/958* (2013.01); *A61M 25/104* (2013.01); *A61B 8/12* (2013.01); *A61M 2025/1079* (2013.01)

(58) Field of Classification Search
CPC ........... A61B 6/481; A61B 6/12; A61B 6/504; A61B 8/12; A61B 8/0891; A61F 2/958; A61M 25/104; A61M 2025/1079
See application file for complete search history.

(56) References Cited

U.S. PATENT DOCUMENTS

| | | | |
|---|---|---|---|
| 10,561,827 B2* | 2/2020 | Tal | A61B 17/1204 |
| 10,736,593 B2* | 8/2020 | Yao | A61B 6/022 |

(Continued)

FOREIGN PATENT DOCUMENTS

| | | | | |
|---|---|---|---|---|
| WO | WO-2017192912 A1 * | 11/2017 | ....... | A61B 17/12031 |
| WO | WO-2019034778 A1 * | 2/2019 | ......... | A61B 17/0057 |

OTHER PUBLICATIONS

Bill D Gogas, The ABSORB bioresorbable vascular scaffold: an evolution or revolution in interventional cardiology?, Hellenic J Cardiol. (Year: 2012).*

(Continued)

*Primary Examiner* — Pascal M Bui Pho
*Assistant Examiner* — Taylor Deutsch
(74) *Attorney, Agent, or Firm* — Kunzler Bean & Adamson

(57) ABSTRACT

The invention provides a method and system for performing angiography and angioplasty within lumen of a blood vessel. To perform angiography, a soft angiography balloon is glided over an angiography guide wire up to a target site through the support of a guide catheter. Subsequently, the soft angiography balloon is inflated at very low pressure 1-2 atmospheres atraumatically, using one or more inflation mechanisms to record one or more angiographic pictures of an internal shape of the lumen. Next, an angioplasty with or without metallic stent or BVS is performed at the target site, and luminal gain is confirmed by repeating soft balloon angiography by re-inflating the soft angiography balloon in a way similar to IVUS or but superior to OCT for metallic stent. Further, a nephrotoxic contrast agent is fully withdrawn from the balloon and it does not pass through the kidneys, thus preventing renal side effects.

12 Claims, 21 Drawing Sheets

(56) References Cited

U.S. PATENT DOCUMENTS

| | | | | |
|---|---|---|---|---|
| 2003/0199767 | A1* | 10/2003 | Cespedes | A61B 5/01 |
| | | | | 600/473 |
| 2007/0173919 | A1* | 7/2007 | Maschke | A61B 5/02007 |
| | | | | 623/1.11 |
| 2009/0234445 | A1* | 9/2009 | Maschke | A61B 5/02007 |
| | | | | 623/2.11 |
| 2011/0112400 | A1* | 5/2011 | Emery | A61N 7/00 |
| | | | | 601/3 |
| 2012/0143054 | A1* | 6/2012 | Eaton | A61M 25/104 |
| | | | | 604/101.02 |
| 2020/0268242 | A1* | 8/2020 | Magaraggia | A61B 1/0011 |
| 2021/0046295 | A1* | 2/2021 | Feng | A61M 25/10185 |
| 2021/0154448 | A1* | 5/2021 | Hodgson | A61M 25/10184 |
| 2021/0346657 | A1* | 11/2021 | Murphy | A61M 25/104 |

OTHER PUBLICATIONS

Jie Wang, Invariant features-based automated registration and montage for wide-field OCT angiography, Biomedical Optics Express (Year: 2019).*

* cited by examiner

METHOD FOR PERFORMING ANGIOGRAPHY AND ANGIOPLASTY WITHIN LUMEN OF A BLOOD VESSEL

FIELD OF THE INVENTION

The invention generally relates to a method for performing angiography within lumen of a blood vessel at a target site using a soft angiography balloon instead of injecting a strong dye directly into the blood vessel as excretion of dye through the kidneys has injurious effect to the extent that it may lead to Acute Renal Failure in some patients. More specifically, the invention relates to a method for confirming the anatomy of the lumen including any change in dimension, reduction in size or position of an angioplasty balloon, metallic stent or Bioabsorbable Vascular Scaffold (BVS), based on position of the soft angiography balloon parked at the target site within lumen of the blood vessel.

BACKGROUND OF THE INVENTION

Angiography is a medical imaging technique, which is used to visualize internal parts of blood vessels and organs of a body such as, but not limited to, lumen of arteries, veins and heart chambers. Various examples of angiography include, but need not be limited to, coronary angiography, cerebral angiography, renal angiography, neuro-vascular angiography, and peripheral angiography. For instance, coronary angiography is performed to obtain an angiographic picture of a lumen of the coronary artery.

Conventionally, coronary angiography is performed by injecting a contrast agent into a lumen near a target site in the artery. The contrast agent makes the lumen of the arteries/veins visible when X-rays are passed through the body, to capture angiographic pictures of the vessel/artery. The angiographic pictures depict the lumen of the arteries or veins near the target site and the exact position of the target site. The target site may include, but is not limited to plaques, blockages in a blood vessel, positioning of the metallic stent or Bioabsorbable Vascular Scaffold (BVS) and adequacy of their deployment.

Also, the contrast agents having radio opacity are used to obtain the angiographic pictures using X-ray imaging of the target site. Various types of contrast agents may include, but need not be limited to, iodinated agents, high osmolar ionic agents, low osmolar non-ionic agents, and barium-based agents (for gastro-intestinal imaging). However, the contrast agents injected into the lumen produce cardiac and renal side effects due to the iodine content, biochemical structure, hydrophilic, lipophilic character, and range of osmolality of the contrast agents.

To reduce the side effects associated with the conventional ionic contrast agents, non-ionic low-osmolar contrast agents and non-ionic iso-osmolar contrast agents are used. However, the non-ionic low-osmolar contrast agents and the non-ionic iso-osmolar contrast agents are not able to eliminate the renal side effects completely. Pretreatment with hydration using normal saline, N-acetylcysteine, theophylline, fenoldopam, and other agents are also used as preventive strategies for avoiding Contrast-Induced Nephropathy (CIN). However, these preventive strategies are also not able to eliminate the renal side effects in all patients.

The major side effects produced by the contrast agents are anaphylactic reactions, Contrast Induced Nephropathy (CIN) and Acute Renal Failure (ARF). CIN is defined as an increase in serum creatinine greater than 25% or more than 44.2 μmol/L (0.5 mg/dL) within three days of intravascular contrast administration in the absence of an alternative cause. CIN is one of the most common causes of newly developed acute renal failures in hospitalized patients following contrast usage. CIN develops in about 5% of patients with normal renal function who are exposed to the contrast agents during angiography procedures. Further, the incidences of CIN may be as high as 25% in patients with preexisting renal impairment, diabetes, hypertension, congestive heart failure, advanced age, and in patients exposed to concurrent administration of nephrotoxic drugs.

Erstwhile techniques include carbon dioxide angiography which is used to avoid renal damage that is otherwise associated with angiography techniques, wherein instead of a contrast agent, radio-opaque carbon dioxide is administered into the lumen. However, carbon dioxide angiography requires a dedicated hardware set-up and training is required for a person handling the apparatus. Additionally, carbon dioxide angiography is associated with a risk of cerebral gas embolization and cerebrovascular accidents. Thus, conducting carbon dioxide angiography procedures such as coronary angiography, cardiac angiography, and angiography in a vessel above the descending aorta is not safe.

Furthermore, the currently used angiography system has limitation specially in high risk patients with impaired Renal function. This was an impetus to develop an apparatus which can perform angiography simply and safely in such conditions.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the invention.

Figure 1:
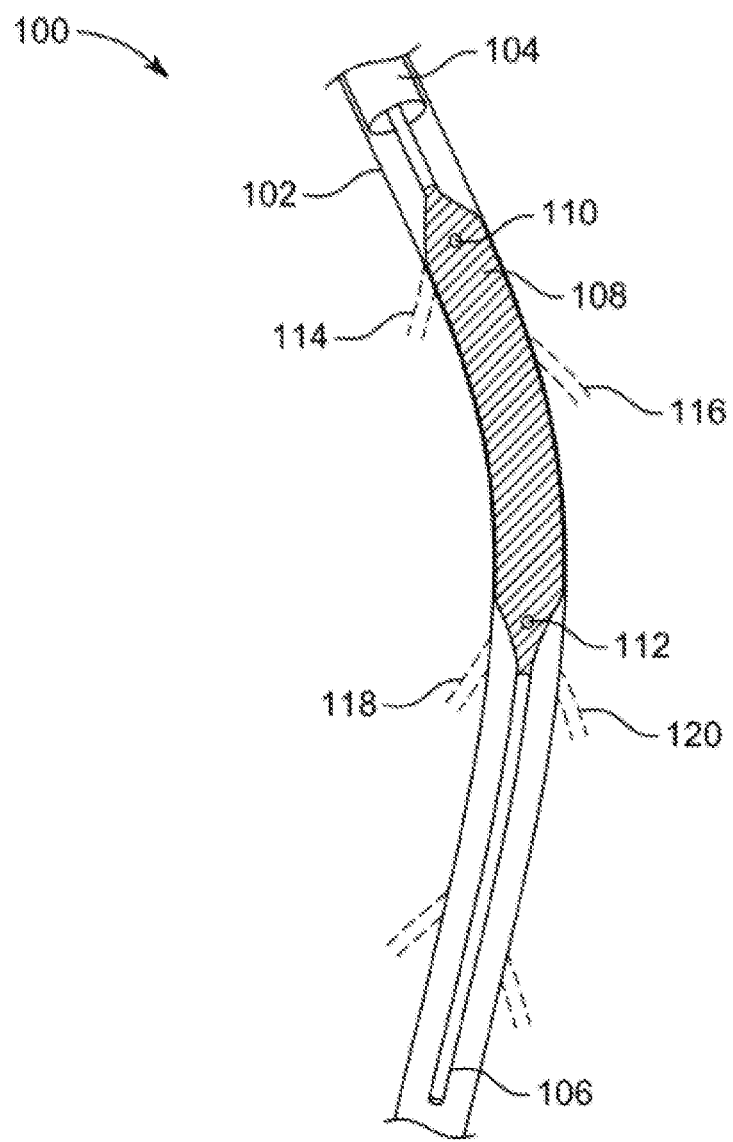
FIG. 1 illustrates an apparatus for performing angiography within lumen of a normal blood vessel by placing a soft angiography balloon at proximal part of the blood vessel, wherein the length of the vessel covered is shown between the known distance of two markers proximal and distal in accordance with an embodiment of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

DETAILED DESCRIPTION OF THE INVENTION

Before describing in detail embodiments that are in accordance with the invention, it should be observed that the embodiments reside primarily in combinations of apparatus components and usage steps relate to performing angiography within lumen of a blood vessel using a soft angiography balloon and confirming the anatomy of the vessel, including lumen diameter, length, any stenosis or expansion, without injecting any contrast material into the vessel for avoiding any excretion of contrast agents through the kidneys and risk of Contrast Induced Nephropathy(CIN). Additionally, said angiography technique helps in stenting procedure by confirming the luminal gain, in obtaining perfect final results.

Accordingly, the apparatus components and method steps have been represented where appropriate by conventional symbols in the drawings, showing only those specific details that are pertinent to understanding the embodiments of the invention so as not to obscure the disclosure with details that will be readily apparent to those of ordinary skill in the art having the benefit of the description herein.

In this document, related terms such as first and second, top and bottom, proximal and distal and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article or composition that comprises a list of elements does not include only those elements but may include other elements not expressly listed or inherent to such process, method, article or composition. An element proceeded by "comprises . . . a" does not, without more constraints, preclude the existence of additional identical elements in the process, method, article or composition that comprises the element.

Various embodiments of the invention provide a method and system for performing angiography and angioplasty within lumen of a blood vessel. The invention provides a method for performing angiography within lumen of a blood vessel using a soft angiography balloon threaded or glided over an angiography guide wire which is moved towards a target site through the support of a guide catheter. Subsequently, the soft angiography balloon is inflated by injecting contrast agent at the target site using one or more inflation mechanisms and with the passage of X-Rays, to record one or more angiographic pictures of an internal shape of the lumen. In response to recording the one or more angiographic pictures, the soft angiography balloon is deflated, and parked at the position in the target site.

Upon verifying the one or more angiographic pictures, if angioplasty is needed then in an ensuing step, an angioplasty balloon is advanced over an angioplasty guide wire, towards the target site based on the position of the soft angiography balloon through the guide catheter. The position of the angioplasty balloon is confirmed by re-inflating the soft angiography balloon by injecting contrast agent using the one or more inflation mechanisms. After completion of angioplasty, the gain in lumen is evaluated by re-inflating the soft angiography balloon catheter by injecting the contrast agent. Later, the iodinated contrast dye, injurious to the body including kidneys is completely withdrawn from the soft angiography balloon without leaving any part in the vessel or in the body thus protecting the kidneys mainly.

Similar steps are repeated when a metallic stent is deployed. In addition, the guide wire is advanced further in the vessel beyond the target site and soft angiography balloon is then re-advanced through the deployed metallic stent, which evaluates the optimal deployment of the metallic stent or even Bioabsorbable vascular scaffold (BVS), equally well without requiring additional hardware or software. The deflated soft angiography balloon is injected with a contrast agent to confirm the internal lumen of the vessel or artery with passage of X-Rays, where the length of the artery is covered by sequential imaging from proximal to distal end of the artery/vessel. Further, a trained physician can view arterial boundaries, the lumen, its stenotic site if any, which requires an interventional correction. Upon determining the position of the stenotic site, the physician can place another metallic stent by confirming the internal diameter of the artery from the proximal end to the distal end of the artery.

FIG. 1 illustrates an apparatus 100 for performing angiography within lumen of a normal blood vessel 102 by placing a soft angiography balloon 108 at proximal part of blood vessel 102, wherein the length of blood vessel 102 covered is shown between the known distance of two markers proximal 110 and distal 112 in accordance with an embodiment of the invention.

As illustrated in FIG. 1, apparatus 100 is inserted into the lumen of blood vessel 102 which may include, but need not be limited to, arteries such as, but not limited to, coronary artery, renal artery, carotid arteries internal or external, vertebral, iliacs internal/external, femoral, posterior tibial, dorsalis pedis, subclavian, innominate, axillary, radial, ulnar, aorta and the like and veins to perform angiography. Apparatus 100 includes a guide catheter 104, and soft angiography balloon 108 mounted on an angiography guide wire 106.

In order to perform angiography within lumen of blood vessel 102, guide catheter 104 and angiography guide wire 106 are inserted into the lumen to reach a target site inside the lumen. The target site may include, but need not be limited to, one or more plaques, one or more swellings, one or more blockages, one or more unexpanded metallic stents or a Bioabsorbable vascular Scaffold (BVS) or dilatations or ectasia in blood vessel 102. Subsequently, angiography guide wire 106 is inserted into the lumen by placing guide catheter 104 at the opening or mouth of blood vessel 102 or closer to the target site inside blood vessel 102. Angiography guide wire 106 may include, but need not be limited to, a thin coronary guide wire and the like. The diameter range of angiography guide wire 106 can be, but need not be limited to, 0.009" to 0.018" (inches).

Guide catheter 104 is placed at the mouth of blood vessel 102 or inside blood vessel 102 for accessing the target site and soft angiography balloon 108 threaded on angiography guide wire 106 is moved towards the target site to reach the target site within the lumen of blood vessel 102.

Soft angiography balloon 108 is made of a material including, but need not be limited to, a soft, flexible, highly complaint, Polyether-Block Amide (PEBEX), Poly Urethane 40-200, Poly Vinyl Chloride (PVC), Polyethylene Terephthalate (PET), and the like. The soft highly compliant material used for soft angiography balloon 108, analyzes the size of the lumen and acquires the shape of blood vessel 102, which can be, but need not be limited to stenosed, narrowed, ectaic or aneurysmal dilatation of the artery, vein, other tubular structures, and the like. Soft angiography balloon 108 is fully expanded even at low 1-2 atmospheric pressures without injuring blood vessel 102.

Once soft angiography balloon 108 reaches the target site, soft angiography balloon 108 is inflated by injecting contrast agent using one or more inflation mechanisms to record one or more angiographic pictures of an internal shape of the lumen. The one or more inflation mechanisms may include, but need not be limited to, one of a radio opaque contrast agent which is injected into soft angiography balloon 108 to inflate soft angiography balloon 108 for recording one or more angiographic pictures of the internal shape of the lumen.

The contrast agent includes, but is not limited to, one or more of iodinated agents, high osmolar ionic agents, low osmolar non-ionic or iso-osmolar agents and barium-based agents. The average amount of contrast agent injected into soft angiography balloon 108 can be, but need not be limited to, 10 ml to 20 ml in coronary or peripheral vasculature and patients with compromised renal function. Also, the one or more angiographic pictures are obtained by passage of X-Rays, upon inflating soft angiography balloon 108, soft angiography balloon 108 adapts to the internal shape of the lumen and records a trace of the contrast agent inside soft angiography balloon 108 and the one or more angiographic pictures facilitate locating the target site.

In accordance with an embodiment, soft angiography balloon 108 is placed at proximal end of the lumen of normal vessel, where the length of blood vessel 102 covered is same as between the known distance of two markers proximal marker 110 and distal marker 112 in FIG. 1. The distance of balloon markers from proximal marker 110 at first position to distal marker 113 on second position in FIG. 2, indicates the total length of the target site. The process of reaching the target sites in multiple locations within the lumen of blood vessel 102 is further described in detail in conjunction with FIG. 2 and FIG. 3.

In comparison to standard angiography where contrast or dye delivered into blood vessel 102 mixes with blood, and with circulation spreads to a plurality of branches 114, 116, 118, and 120, in the angiography procedure using soft angiography balloon 108, the contrast or dye is limited within the balloon. Furthermore, the standard angiography procedure mainly studies the major branch, while soft angiography balloon 108 studies each branch of plurality of branches 114, 116, 118 and 120 when individually cannulated with the help of angiography guide wire 106.

Figure 2:
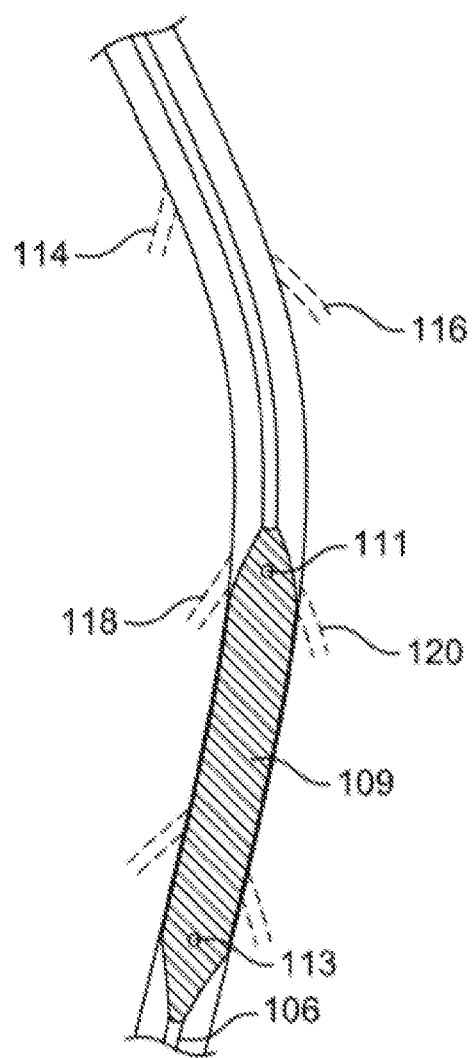
FIG. 2 illustrates the placement of the soft angiography balloon at distal part of the normal blood vessel, wherein the length of the vessel covered is shown between the known distance of two markers proximal and distal in accordance with an embodiment of the invention.

As illustrated in FIG. 2, a soft angiography balloon 109 is advanced in deflated state over angiography guide wire 106 to one or more distal positions of the lumen and inflated by injecting contrast agent at low pressure, where the length of blood vessel 102 covered is same as between the known distance of two markers proximal 111 and distal 113.

Figure 3:
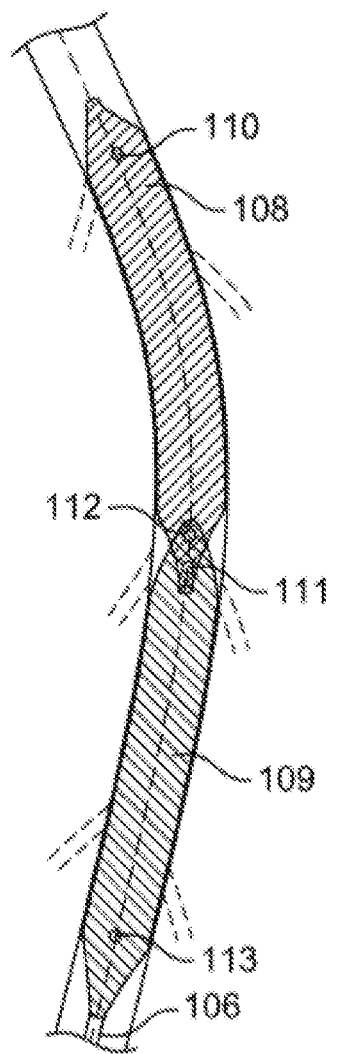
FIG. 3 illustrates the placement of the soft angiography balloon at first position and at second position of the blood vessel depicted in FIG. 1 and FIG. 2, wherein the longer length of the vessel covered is shown between the known distance of the proximal marker at first position and the distal marker at the second position, using a computer application of superimposing two images in accordance with an embodiment of the invention.

FIG. 3 illustrates the placement of soft angiography balloon 108 at a first position of blood vessel 102 depicted in FIG. 1 and FIG. 2, wherein the longer length of blood vessel 102 covered is shown between the known distance of proximal marker 110 at first position to distal marker 113 at second position using a computer application of superimposing two images to analyze the longer segment of blood vessel 102.

Once soft angiography balloon 108 is positioned at the target site, soft angiography balloon 108 is inflated by injecting contrast agent at low pressure using the one or more inflation mechanisms to record one or more angiographic pictures of the internal shape of the lumen. The process of recording one or more angiographic pictures at plurality of target sites inside the lumen of blood vessel 102 is detailed in conjunction with FIG. 4, FIG. 5 and FIG. 6.

Figure 4:
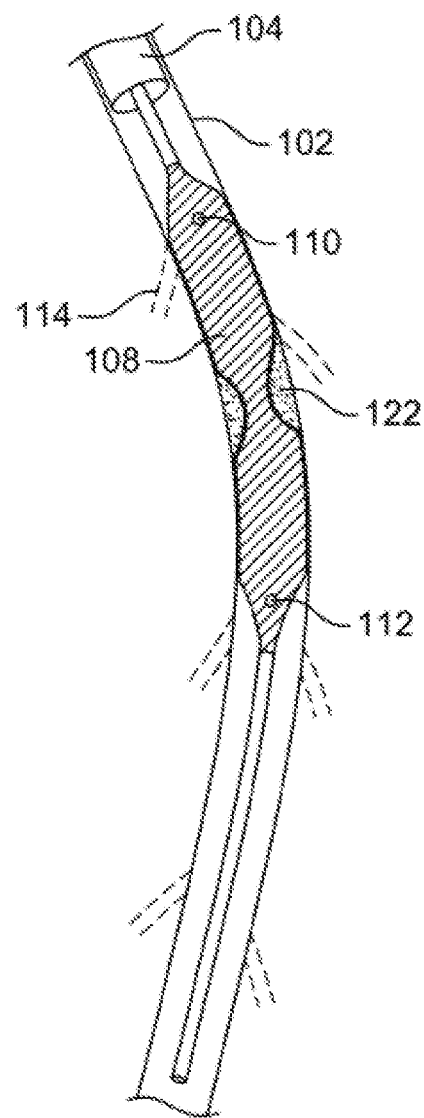
FIG. 4 illustrates the process of recording one or more angiographic pictures using the apparatus based on a position of the soft angiography balloon at proximal target site with atherosclerotic plaque stenosis inside the lumen of the blood vessel in accordance with an exemplary embodiment of the invention.

FIG. 4 illustrates the process of recording one or more angiographic pictures using apparatus 100 soft angiography balloon 108 threaded over angiography guide wire 106 is advanced towards proximal target site 122 inside the lumen of blood vessel 102, where proximal target site 122 can be, but need not be limited to, an atheromatous narrowing formed inside the lumen of blood vessel 102. Once soft angiography balloon 108 reaches proximal target site 122, soft angiography balloon 108 is inflated by injecting contrast agent at low pressure using the one or more inflation mechanisms to record one or more angiographic pictures of the internal shape of the lumen. The one or more inflation mechanisms may include, but need not be limited to, injecting one of a radio opaque contrast agent into soft angiography balloon 108 in accordance with an exemplary embodiment of the invention.

Figure 5:
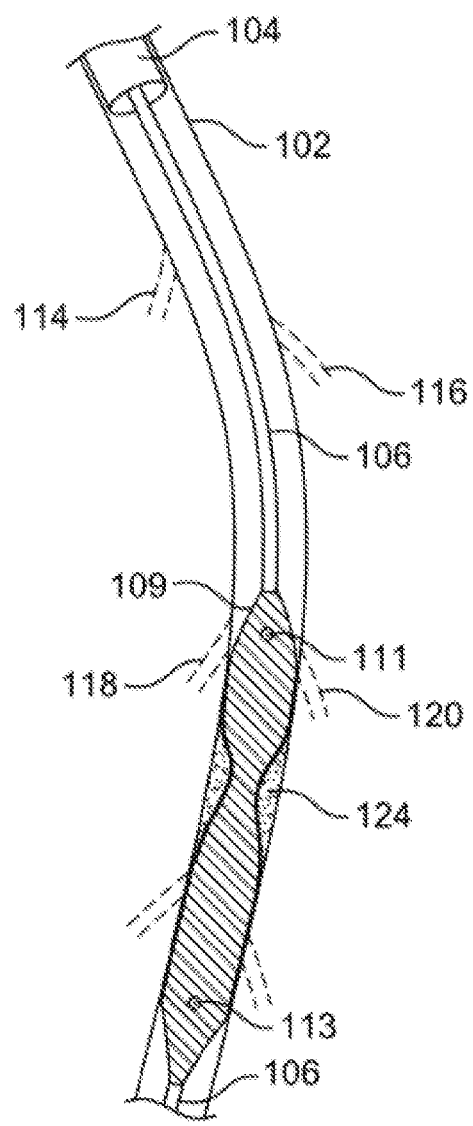
FIG. 5 illustrates the process of recording one or more angiographic pictures using the apparatus based on a position of the soft angiography balloon at distal target site with atherosclerotic plaque stenosis inside the lumen of the blood vessel in accordance with an exemplary embodiment of the invention.

In response to recording the one or more angiographic pictures at proximal target site 122, soft angiography balloon 108 is deflated by removing the contrast agent and advanced towards second distal target site 124 detailed in conjunction with FIG. 5.

FIG. 5 illustrates the process of recording one or more angiographic pictures using apparatus 100, soft angiography balloon 109 is advanced towards distal target site 124 at the distal end of the lumen of blood vessel 102 and inflated by injecting contrast agent at low pressure based on one or more markers 111 and 113 on soft angiography balloon 109, wherein distal target site 124 can be, but need not be limited to, an atheromatous plaque formed inside the lumen of blood vessel 102 in accordance with an exemplary embodiment of the invention.

Once soft angiography balloon 109 reaches distal target site 124, soft angiography balloon 109 is re-inflated by injecting contrast agent at low pressure to record one or more angiographic pictures of the internal shape of lumen. The one or more angiographic pictures may include, but need not be limited to, one or more positions to cover the area of interest or whole length of blood vessel 102. Therefore, the one or more angiographic pictures recorded at multiple positions inside the lumen of blood vessel 102 are analyzed to identify target narrowing or narrowings, magnitude of severity and length of narrowed segment of blood vessel 102 for performing angioplasty. Accordingly, soft angiography balloon 108 in FIG. 4 and soft angiography balloon 109 in FIG. 5 is parked at the position on the target site or sites and the process of performing angioplasty at the target site or sites is further detailed in conjunction with FIG. 7.

Figure 6:
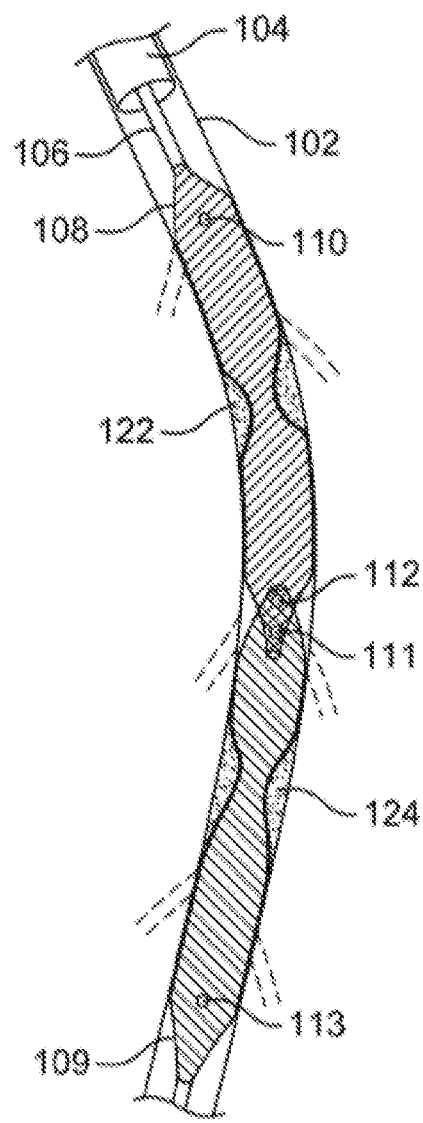
FIG. 6 illustrates the process of recording one or more superimposed angiographic pictures at the atherosclerotic plaques at target sites located at the proximal end and the distal end of the blood vessel respectively using the soft angiography balloon, in accordance with an exemplary embodiment of the invention, wherein both pictures are shown after superimposition of FIG. 4 and FIG. 5 to cover a larger area and both targets.

FIG. 6 illustrates the process of recording one or more superimposed angiographic pictures at the atherosclerotic plaques target sites located at proximal end 122 and distal end 124 of blood vessel 102 using soft angiography balloon 108 in accordance with an exemplary embodiment of the invention, wherein both pictures are shown after superimposition of FIG. 4 and FIG. 5 to cover a larger area and both targets.

As illustrated in FIG. 6, soft angiography balloon 108 positioned at proximal end 122 and soft angiography balloon 109 positioned at distal end 124 of the lumen of blood vessel 102 records one or more superimposed angiographic pictures at the target sites located at proximal end 122 and distal end 124 of blood vessel 102. Subsequently, proximal marker 110 of soft angiography balloon 108 at first position 122 to distal marker 113 of soft angiography balloon 109 at second position 124 covers the longer length of blood vessel 102 with both the target sites 122 and 124.

Further, the one or more angiographic pictures recorded at the respective target site 122 and 124 are stitched sequentially, arranged and superimposed to cover longer length of blood vessel 102, where the recorded angiographic pictures become comparable to standard benchmark angiography, without spilling any contrast agent into human body, and avoiding any systemic or kidney damage.

Figure 7:
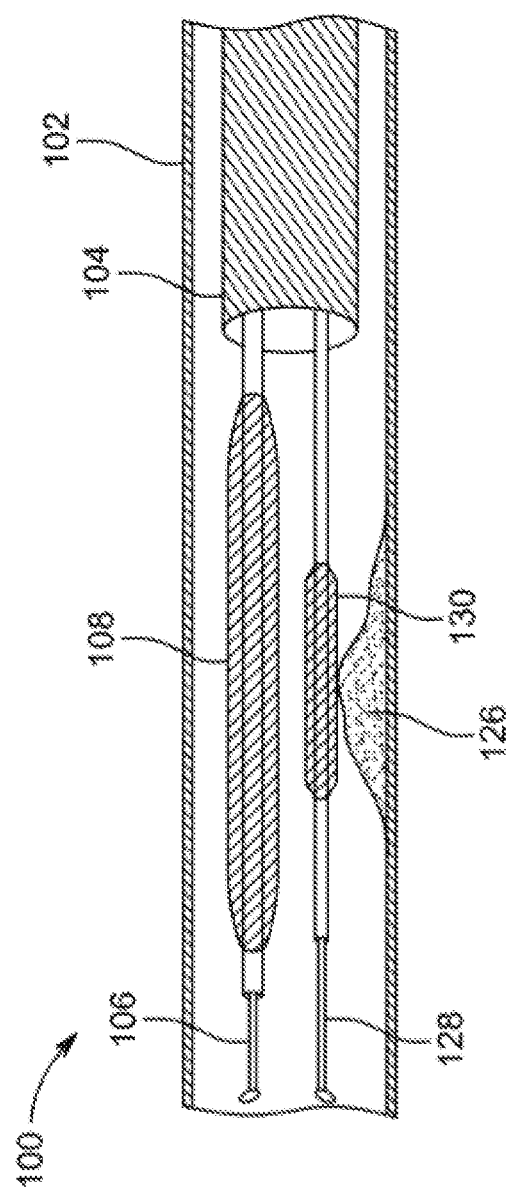
FIG. 7 illustrates the process of performing Plain Old Balloon Angioplasty (POBA) at a target site with atheromatous plaque and narrowing, inside the lumen of the blood vessel while advancing the high pressure non-compliant POBA balloon over an angioplasty guide wire using the apparatus in accordance with an embodiment of the invention.

FIG. 7 illustrates the process of performing Plain Old Balloon Angioplasty (POBA) at a target site 126 with atheromatous plaque and narrowing, inside the lumen of the blood vessel 102 while advancing the POBA balloon over an angioplasty guide wire 128 using apparatus 100 in accordance with an embodiment of the invention.

As illustrated in FIG. 7, apparatus 100 includes guide catheter 104, angiography guide wire 106 threaded with soft angiography balloon 108, and an angioplasty balloon 130 threaded over an angioplasty guide wire 128.

Upon identifying target site 126 affected with at least one atheromatous plaque and narrowing inside the lumen of blood vessel 102 using soft angiography balloon 108, angioplasty balloon 130 is inserted through guide catheter 104 and parked at target site 126 for performing angioplasty. The commonly known term in practice, used to perform angioplasty is POBA (Plain Old Balloon Angioplasty), where a narrowed segment of blood vessel 102 with atheromatous plaque encroaching the lumen is compressed by high pressure semi or non-compliant balloon.

Once angioplasty balloon 130 is parked at target site 126, the position of angioplasty balloon 130 is confirmed using soft angiography balloon 108. The process of confirming the position of angioplasty balloon 130 is detailed in conjunction with FIG. 8.

Figure 8:
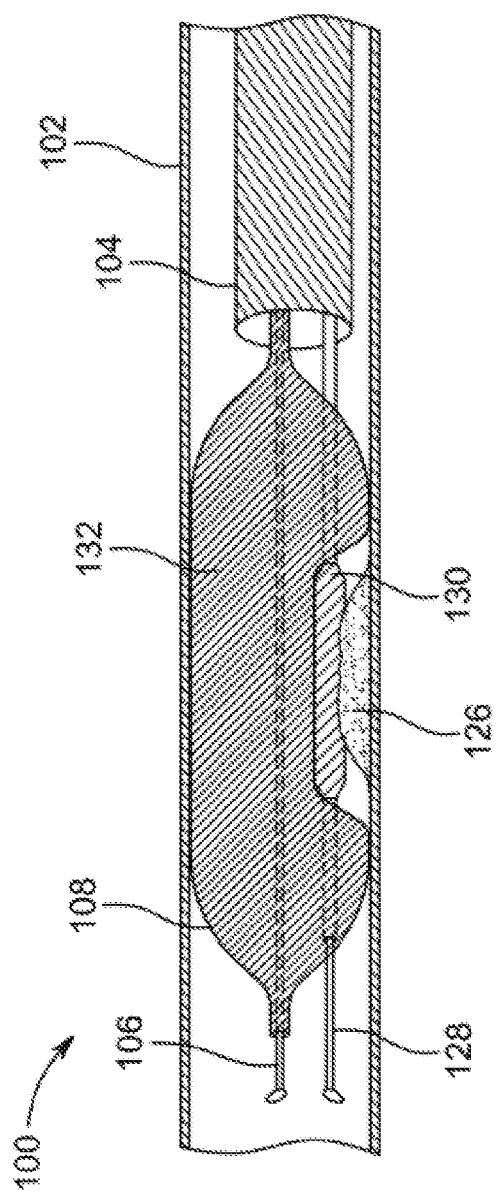
FIG. 8 illustrates the process of confirming the position of high-pressure semi compliant angioplasty balloon in relation to the target site inside the lumen of the blood vessel by inflating the soft angiography balloon with a contrast agent or dye at low pressure, using the apparatus in accordance with an embodiment of the invention.

FIG. 8 illustrates the process of confirming the position of high-pressure semi compliant angioplasty balloon 130 in relation to target site 126 inside the lumen of blood vessel 102 by inflating soft angiography balloon 108 with a contrast agent or dye 132 at low pressure, using apparatus 100 in accordance with an embodiment of the invention.

As illustrated in FIG. 8, the position of angioplasty balloon 130 is confirmed by re-inflating soft angiography balloon 108 parked at target site 126 using the one or more inflation mechanisms. The one or more inflation mechanisms may include, but need not be limited to, filling contrast agent or dye 132 at low pressure into soft angiography balloon 108.

Upon re-inflating soft angiography balloon 108 by injecting contrast agent at low pressure at target site 126, soft angiography balloon 108 configures itself to adapt to the internal shape of the lumen along with the position of angioplasty balloon 130 in relation to target site 126 affected with atheromatous or narrowing, without compressing or altering the internal shape of the lumen using a very soft and highly compliant nature of the balloon material which is capable of fully expanding at low pressure 1-2 atmospheres (atm.).

Figure 9:
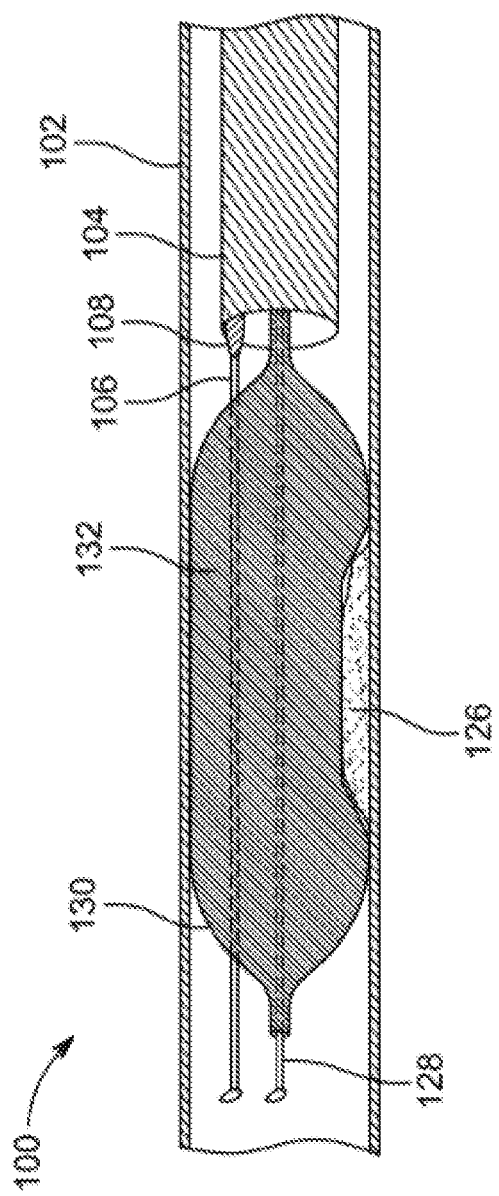
FIG. 9 illustrates the process of performing angioplasty by inflating the high-pressure angioplasty balloon to compress atheroma at the target site inside the lumen of the blood vessel using the apparatus in accordance with an embodiment of the invention.

FIG. 9 depicts the position of angioplasty balloon 130 in relation to target site stenosis 126 which is confirmed by inflating soft angiography balloon 108 by injecting contrast agent at low pressure. The process of angioplasty is performed by inflating the high-pressure angioplasty balloon 130 to compress atheroma at target site 126 inside the lumen of blood vessel 102 using apparatus 100 in accordance with an embodiment of the invention.

As illustrated in FIG. 9, angioplasty balloon 130 is inflated using the one or more inflation mechanism upon confirming the position of angioplasty balloon 130, which may include, but need not be limited to a high pressure semi compliant angioplasty balloon. The one or more inflation mechanisms used to inflate angioplasty balloon 130 may include, but need not be limited to, injecting a fluid, diluted contrast agent/dye 132 under adequate pressure of 6-20 atmospheres or more.

Angioplasty balloon 130 is a semi-compliant or non-compliant high-pressure balloon with much higher stiffness as compared to highly compliant soft angiography balloon 108. Once semi or non-compliant angioplasty balloon 130 is inflated, angioplasty balloon 130 compresses atheromatous plaque at target site 126 inside the lumen of blood vessel 102 and expands the narrowed lumen. Upon performing angioplasty, the position of angioplasty or the removal of atheromatous plaque at target site 126 is confirmed by performing soft balloon angiography. The process of performing angiography after performing angioplasty at target site 126 is detailed in conjunction with FIG. 10.

Figure 10:
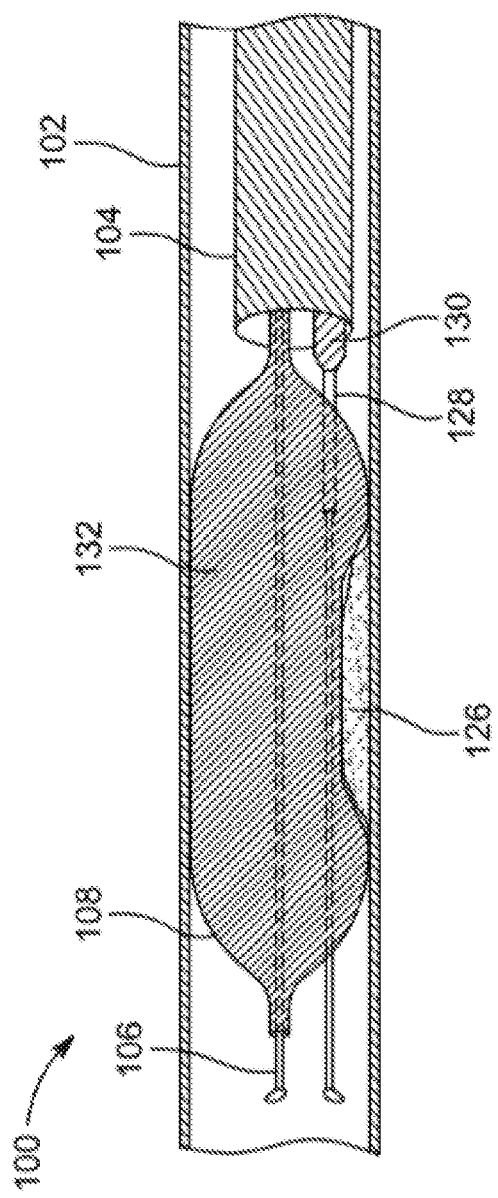
FIG. 10 illustrates the process of performing repeat soft balloon angiography by injecting contrast agent in soft angiography balloon at low pressure within the improved lumen after compressing the atheromatous stenosis at target site, which depicts a successful angioplasty using the high pressure angioplasty balloon, which is withdrawn over the angioplasty guide wire and parked in a guide catheter, using the apparatus in accordance with an embodiment of the invention.

FIG. 10 illustrates the process of performing angiography using soft angiography balloon 108 by injecting contrast agent at low pressure within the improved lumen after compressing the atheromatous plaque/stenosis at target site 126, which depicts a successful angioplasty using the high pressure angioplasty balloon 130, which is withdrawn over angioplasty guide wire 128 and parked in guide catheter 104 using apparatus 100 in accordance with an embodiment of the invention.

Soft angiography balloon 108 upon reaching target site 126 is inflated with one or more inflation mechanisms including a contrast agent 132 to assess internal diameter of blood vessel 102, performance of POBA and compression of atheromatous plaque at target site 126 and luminal gain. Once it is confirmed that atheromatous plaque is fully compressed and flattened out, the successful procedure of performing angioplasty is confirmed and all the hardware are retrieved and removed from the body on completion of POBA procedure.

Figure 11:
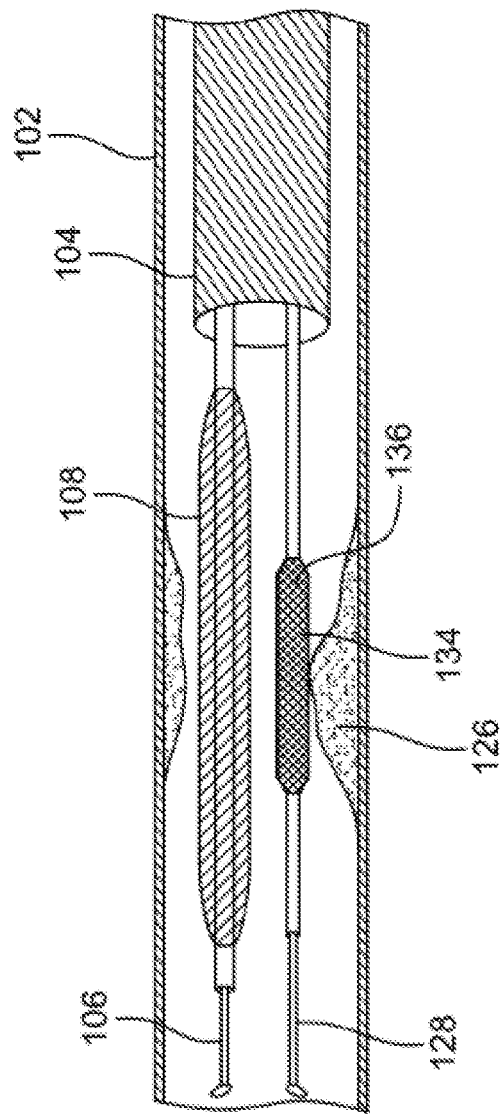
FIG. 11 illustrates the apparatus and its components of pre-mounted metallic stent on a semi-compliant balloon for deployment, along with the soft angiography balloon mounted on an angiography guide wire across the target narrowing caused by atherosclerotic plaque in the blood vessel, in accordance with an embodiment of invention.

FIG. 11 illustrates apparatus 100 and its components for pre-mounted metallic stent 136 on a semi-compliant balloon 134 deployment in accordance with an embodiment of invention.

As illustrated in FIG. 11, apparatus 100 includes a pre-mounted metallic stent 136 over high pressure semi compliant stent balloon 134, for performing angioplasty and stent deployment at target site 126 affected with atheromatous plaque inside the lumen of blood vessel 102. Apparatus 100 also includes soft angiography balloon 108 threaded over angiography guide wire 106 and guide catheter 104 placed in blood vessel 102 to confirm the position of deployment of pre-mounted metallic stent 136 in relation to stenosis. The process of confirming the position of pre-mounted metallic stent 136 at target site 126 is detailed in conjunction with FIG. 12.

Figure 12:
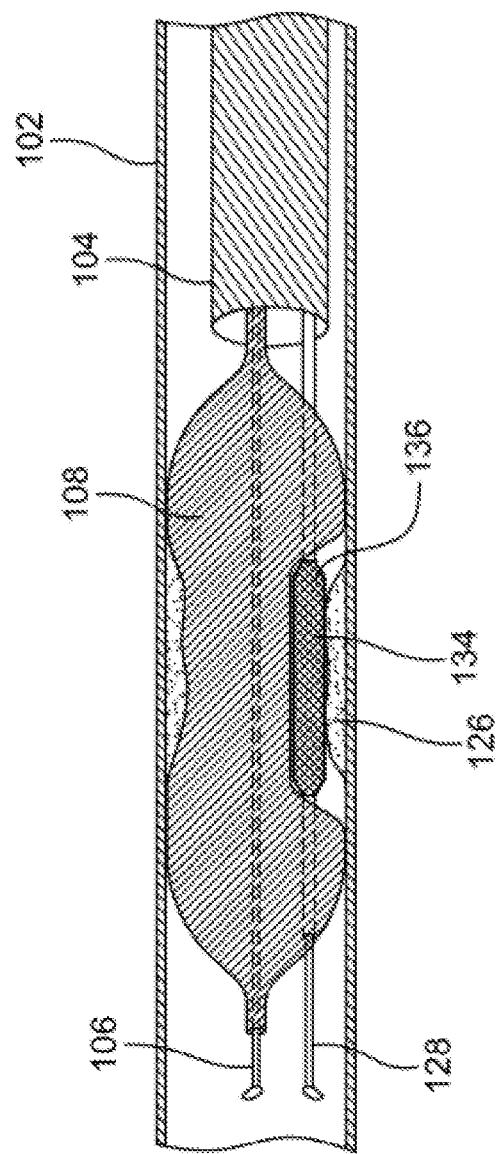
FIG. 12 illustrates the process of recording one or more angiographic pictures by performing soft balloon angiography by injecting contrast or dye in to the soft angiography balloon at the target site affected with stenosis inside the lumen of the blood vessel prior to performing angioplasty with the pre-mounted metallic stent deployment in accordance with an embodiment of the invention.

FIG. 12 illustrates the process of recording one or more angiographic pictures using soft angiography balloon 108 by injecting contrast agent at low pressure at target site 126 affected with stenosis inside the lumen of blood vessel 102 prior to performing angioplasty with pre-mounted metallic stent 136 deployment in accordance with an embodiment of the invention.

As illustrated in FIG. 12, pre-mounted metallic stent 136 over semi-compliant stent balloon 134 is advanced over angioplasty guide wire 126 through guide catheter 104 placed in blood vessel 102 across target site 126 affected with atheromatous plaque. Once semi-compliant stent balloon 134 reaches target site 126, the position of semi-compliant stent balloon 134 is confirmed before deploying pre-mounted metallic stent 136 by advancing soft angiography balloon 108 over angiography guide wire 106.

Moving on, soft angiography balloon 108 is inflated using the one or more inflation mechanisms by injecting contrast agent or dye 132 at low pressure to confirm the position of semi-compliant stent balloon 134 in relation to atheromatous narrowing at target site 126. Upon confirming the position of semi-compliant stent balloon 134, pre-mounted metallic stent 136 is deployed at target site 126. The process of deploying pre-mounted metallic stent 136 is detailed in conjunction with FIG. 13.

Figure 13:
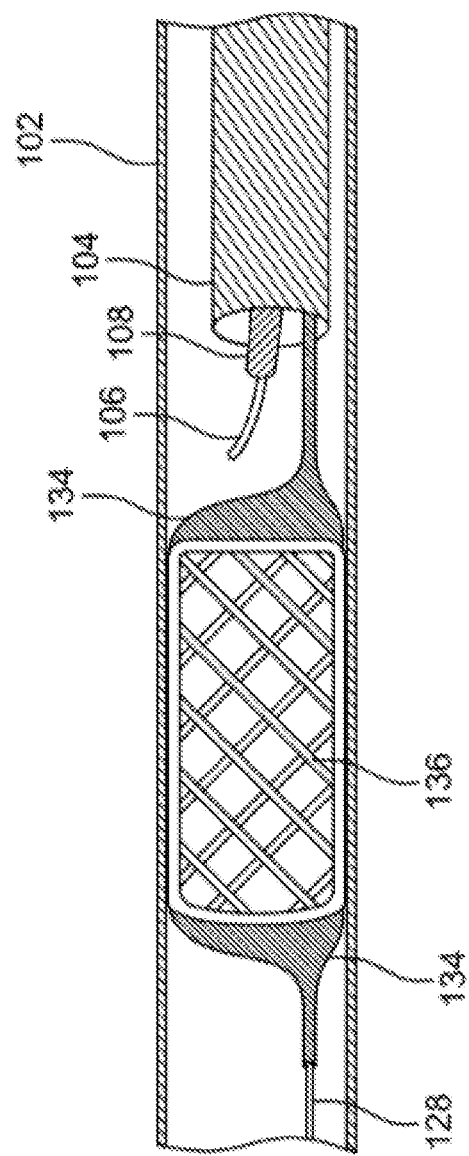
FIG. 13 illustrates the process of the pre-mounted metallic stent deployment at the target site affected with stenosis by inflating the high pressure semi-compliant stent balloon inside the lumen of the blood vessel, while the soft angiography balloon is withdrawn over the angiography guide wire and parked in the guide catheter using the apparatus in accordance with an embodiment of the invention.

FIG. 13 illustrates the process of pre-mounted metallic stent 136 deployment at target site 126 affected with stenosis by inflating high pressure semi-compliant balloon 134 inside the lumen of blood vessel 102, while soft angiography balloon 108 is withdrawn over angiography guide wire 106 and parked in guide catheter 104 using apparatus 100 in accordance with an embodiment of the invention.

Moving on, pre-mounted metallic stent 136 is deployed. Once pre-mounted metallic stent 136 is expanded at target site 126, the position and expansion of pre-mounted metallic stent 136 is verified using soft angiography balloon 108. The process of verifying the position of pre-mounted stent 136 by re-advancing soft angiography balloon 108 over angiography guide wire 106 through the deployed pre-mounted metallic stent 136 using apparatus 100 in accordance with an embodiment of the invention in conjunction with FIG. 14.

Figure 14:
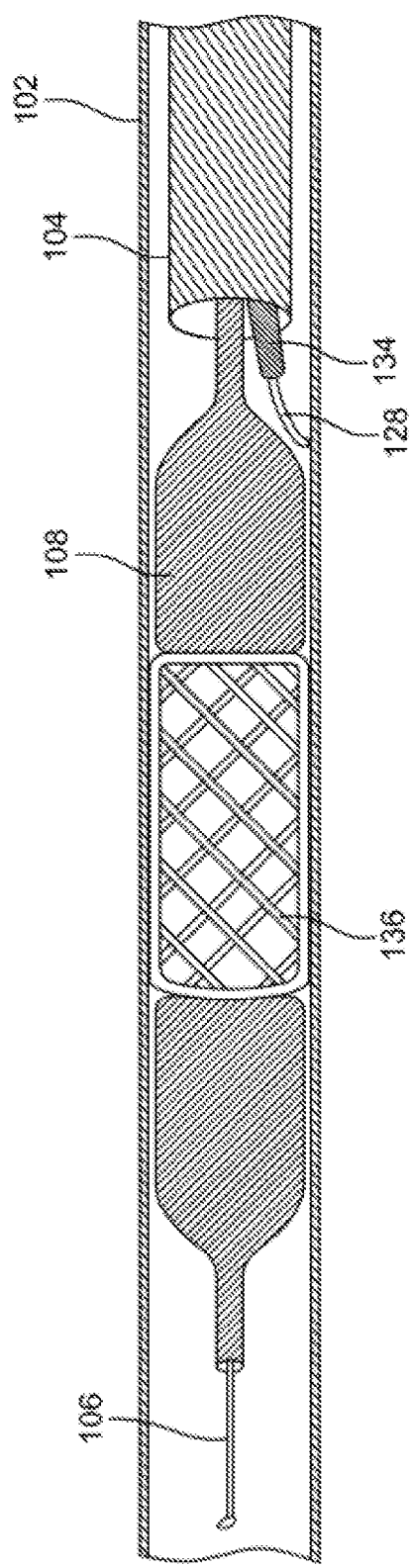
FIG. 14 illustrates the process of verifying the position and expansion of the metallic stent deployment at the target site inside the lumen of the blood vessel by re-advancing the soft angiography balloon through the deployed metallic stent and injecting the contrast agent at low pressure after withdrawing stent balloon back in the guiding catheter, using the apparatus in accordance with an embodiment of the invention.

As illustrated in FIG. 14, soft angiography balloon 108 is inflated at low 1-2 atmospheric pressure using the one or more inflation mechanisms by injecting the contrast agent 132 to confirm the deployment of pre-mounted metallic stent 136 with its full expansion and compression of atheromatous plaque at target site 126.

Figure 15:
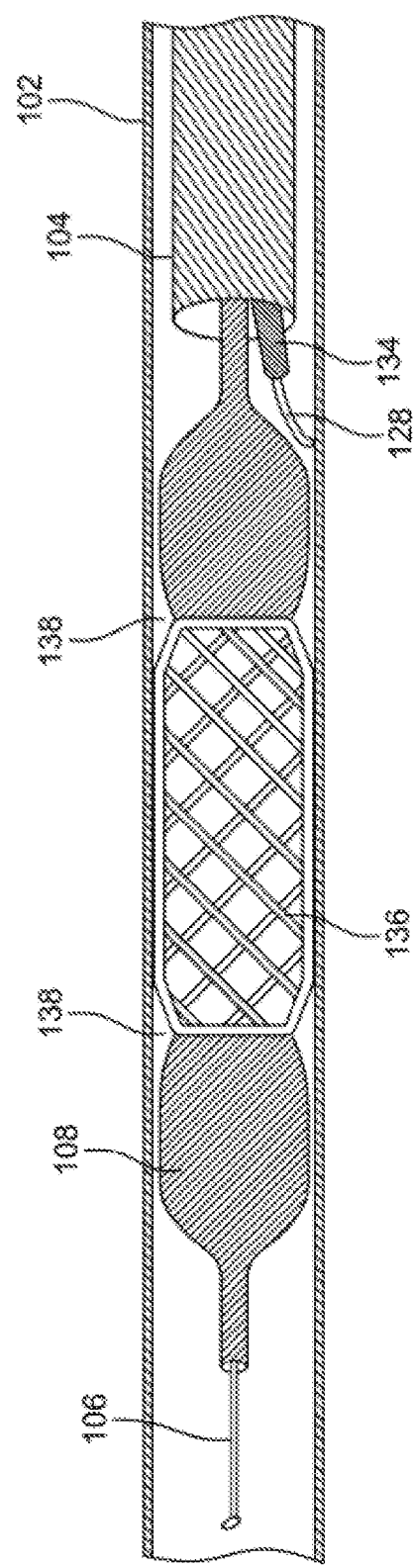
FIG. 15 illustrates the process of confirming the plurality of under expanded ends of the deployed metallic stent by performing soft balloon angiography by injecting contrast agent and inflating the soft angiography balloon at low pressure, after withdrawing the high pressure angioplasty balloon and parking the high pressure angioplasty balloon in the guide catheter, using the apparatus in accordance with an embodiment of the invention.

FIG. 15 illustrates deployment of pre-mounted metallic stent 136, if soft angiography balloon 108 shows under expanded metallic stent 136 based on one or more angiographic pictures.

Plurality of under expanded both ends 138 are caused due to a tough narrowing with fibrosis and calcification, and lead to a poor long-term result of angioplasty with the deployment of metallic stent 136 in accordance with an embodiment of the invention.

Upon confirming the one or more positions of under expanded ends 138 of metallic stent 136, soft angiography balloon 108 is deflated and withdrawn over with angiography guide wire 106 and a high pressure non-compliant angioplasty balloon 140 is advanced over angioplasty guide wire 128, towards one or more portions of under expanded ends 138 of metallic stent 136.

Figure 16:
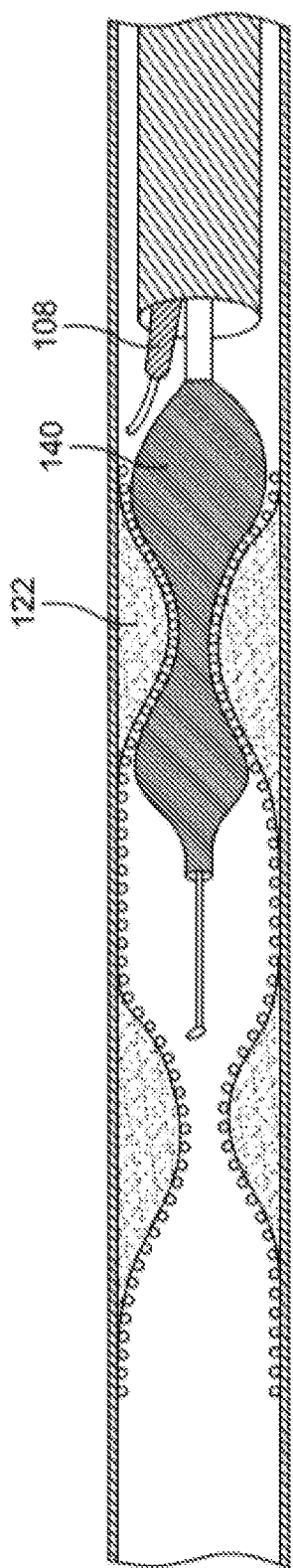
FIG. 16 illustrates the placement of high pressure non-compliant angioplasty balloon across first under expanded end of the metallic stent at the first target site in accordance with an embodiment of the invention.

FIG. 16 illustrates the placement of high pressure non-compliant angioplasty balloon 140 across first under expanded end 138 of metallic stent 136 at first target site 122 and inflated using the one or more inflation mechanisms to perform dilatation by injecting fluid. After dilatation, under deployed metallic stent 136 gets fully expanded as shown in FIG. 17.

Figure 17:
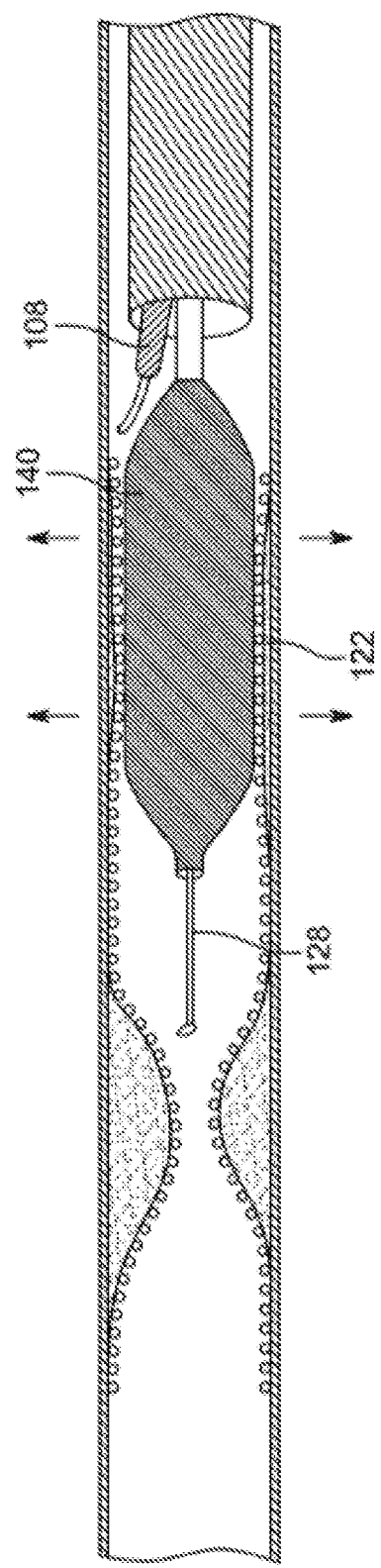
FIG. 17 illustrates the process of inflating the non-compliant angioplasty balloon to fully expand the under deployed metallic stent end by compressing atheromatous plaque at high pressure, at the first target stenosis using the apparatus in accordance with an embodiment of the invention.

FIG. 17 illustrates the process of inflating non-compliant angioplasty balloon 140 at high pressure to fully expand the under deployed metallic stent end 138 by compressing atheromatous plaque at first target stenosis 122 using apparatus 100 in accordance with an embodiment of the invention.

Figure 18:
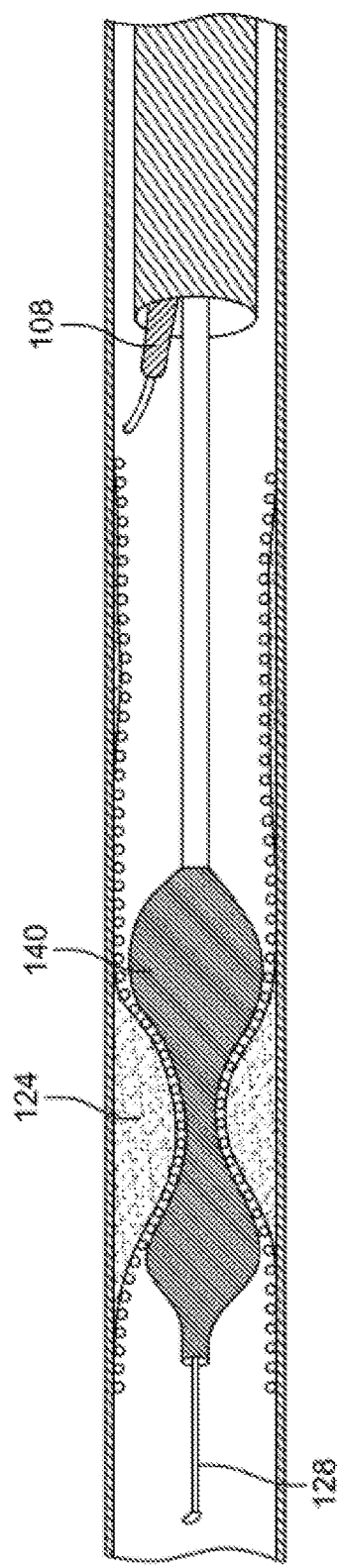
FIG. 18 illustrates the process of advancing the deflated high pressure non-compliant angioplasty balloon across the second target stenosis with under expanded metallic stent using the apparatus in accordance with an embodiment of the invention.

FIG. 18 illustrates high pressure non-compliant angioplasty balloon 140 which is deflated from first target stenosis 122 by removing the contrast agent and further advanced towards second target stenosis 124 with under expanded metallic stent 136's second end 138. Once high pressure non-compliant angioplasty balloon 140 reaches second stenosis 124, non-compliant angioplasty balloon 140 is inflated using the one or more inflation mechanisms by injecting contrast agent 132 at higher pressure to compress the tough plaque stenosis 124 and fully expand stent end 136. The process of inflating high pressure non-compliant angioplasty balloon 140 is detailed in conjunction with FIG. 19.

Figure 19:
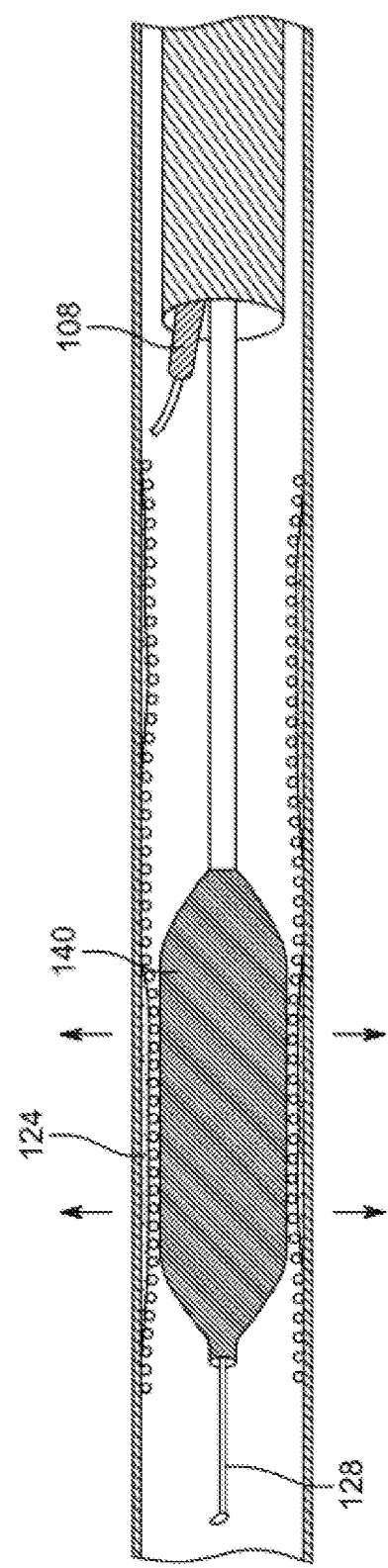
FIG. 19 illustrates the process of inflating the non-compliant angioplasty balloon across the second target stenosis due to the under expanded metallic stent at high pressure for full expansion of the stent using the apparatus in accordance with an embodiment of the invention.

FIG. 19 illustrates the process of inflating high pressure non-compliant angioplasty balloon 140 across second target stenosis 124 due to under expanded metallic stent 138 for full expansion of stent 136 using the apparatus in accordance with an embodiment of the invention.

As illustrated in FIG. 19, non-compliant angioplasty balloon 140 is inflated at higher pressure to compress the tough plaque stenosis 124 for fully expanding under deployed stent end 138. Upon fully expanding deployed metallic stent 136, non-compliant angioplasty balloon 140 is deflated by removing contrast agent 132 and withdrawn into guide catheter 104.

Figure 20:
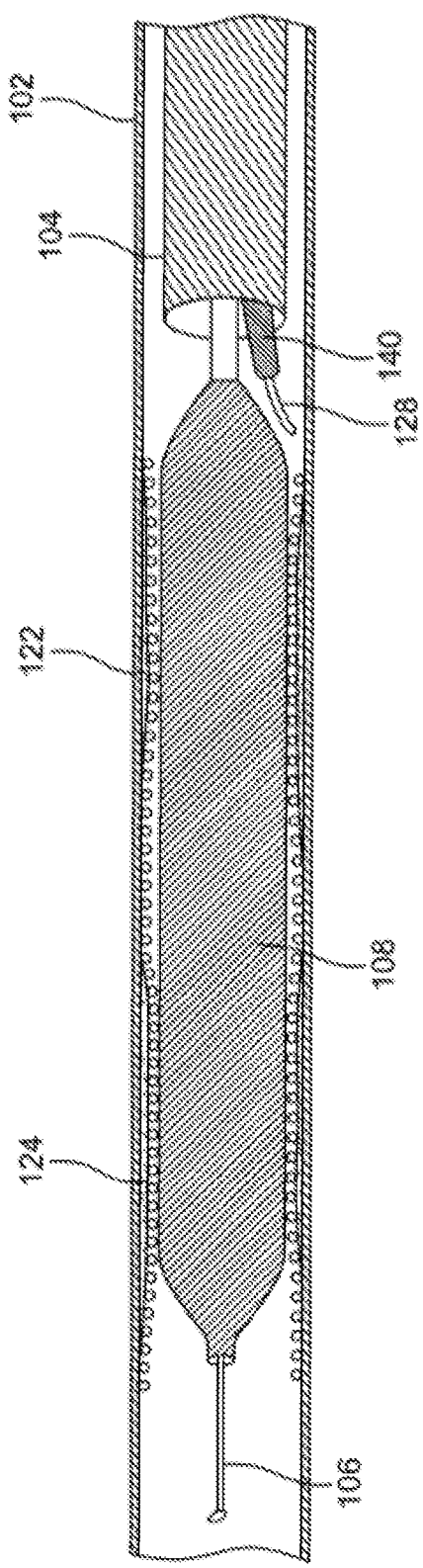
FIG. 20 illustrates the confirmation of full expansion after post dilatation of the deployed metallic stent by performing soft balloon angiography by re-advancing the soft angiography balloon across the target sites and injecting the contrast agent and inflating the soft angiography balloon at low pressure using the apparatus in accordance with an embodiment of the invention.

FIG. 20 illustrates soft angiography balloon 108 with very high compliant properties which is re-advanced towards target sites 122 and 124 and inflated using the one or more inflation mechanisms at very low pressure 1-2 atmospheres, in atraumatic way to confirm the full expansion of deployed stent 136 with luminal gain up to blood vessels normal diameter using apparatus 100 in accordance with an embodiment of the invention.

In accordance with an embodiment, the process of performing angioplasty or stent deployment utilizes other imaging technologies such as, but not limited to, Intra Vascular Ultrasound (IVUS) or Optical Coherence Tomography (OCT).

IVUS utilizes a specialized catheter which is advanced over angiography guide wire 106 in blood vessel 102 for recording one or more IVUS pictures through specialized ultra sound system and displays blood vessel wall, its internal lumen, its deviation from normal structure of the lumen, intimal medial walls, but not limited to, stenosis, dilatations, and plaques are confirmed.

For instance, if blood vessel 102 is detected with two distinct stenosis due to atheromatous plaques, soft angiography balloon 108 is advanced over angiography guide wire 106 and placed in blood vessel 102 at target sites with two atheromatous stenosis. Upon reaching at the target sites, soft angiography balloon 108 is inflated with contrast agent or dye at very low pressure 1-2 atmosphere using the one or more inflation mechanisms atraumatically, where soft angiography balloon 108 is adapts to the shape of the lumen and displays uneven lumen with two distinct narrowings of atheromatous plaques, very similar to IVUS images.

Further, the two distinct atheromatous plaque narrowings identified using soft angiography balloon 108 are treated by performing angioplasty or stent deployment. The stent is placed covering two distinct atheromatous plaque narrowings and the if stent remains under expanded at deployment, similar to which can be clearly assessed by IVUS imaging. Also, the metallic struts of the stent block ultrasound waves and these are reflected as white dots with absence of ultrasound signals.

The IVUS images display two distinct areas of stenosis which are not in line with the anticipated course of blood vessel 102 wall and reflects under expanded stent edges. This help in taking a remediable action to have perfect deployment of result of stent. Similarly, soft angiography balloon 108, when advanced and inflated at the target site with contrast agent at even low pressure of 1-2 atmospheres, soft angiography balloon 108 captures one or more angiography pictures to confirm the non-uniform expansion of the stent at the target sites. Thus, the process of diagnosing the target sites using soft angiography balloon 108 provides information without requiring any exchange or additional hardware for imaging for the efficacy of stent deployment.

Optical Coherence Tomography (OCT) imaging technique is another specialized technique, which utilizes a special probe with light source that is advanced over angiography guide wire 106 through guide catheter 104 in blood vessel 102 to record details of blood vessel 102 wall, its detailed anatomy of the lumen of vessel such as, plurality of target sites insides the lumen. OCT imaging technique uses an optical coherence tomography detector to visualize atheromatous plaques at plurality of target sites 122 and 124 with under expanded ends of metallic stent.

Also, after deploying the metallic stent, special probe is used to display the details of the deployment of a metallic stent which may include, but need not be limited to, full expansion of stent, under expansion of metallic sent and non-metallic Bioabsorbable Vascular Scaffolds (BVS) equally well, whereas BVS are not visualized through IVUS being non-metallic, sound waves are not reflected away or obstructed by Polymer L-Lactide Acid (PLLA) biochemical nonmetallic compound such as, but not limited to, struts of BVS. Further, OCT elegantly displays the confirmation of full expansion of the BVS after high pressure non-compliant angioplasty balloon dilatation.

After Bioabsorbable Vascular Scaffold(BVS), soft angiography balloon 108 inflated with contrast agent even at low pressure atraumatically depicts under expansion of BVS and also after full expansion of device after dilation of high pressure non-compliant angioplasty balloon similar to OCT. Therefore, soft angiography balloon 108 can fulfill the imaging capability of OCT in determining the adequacy of deployment of BVS in addition to metallic stents alike, apparatus 100 in accordance with an embodiment of the invention.

Figure 21:
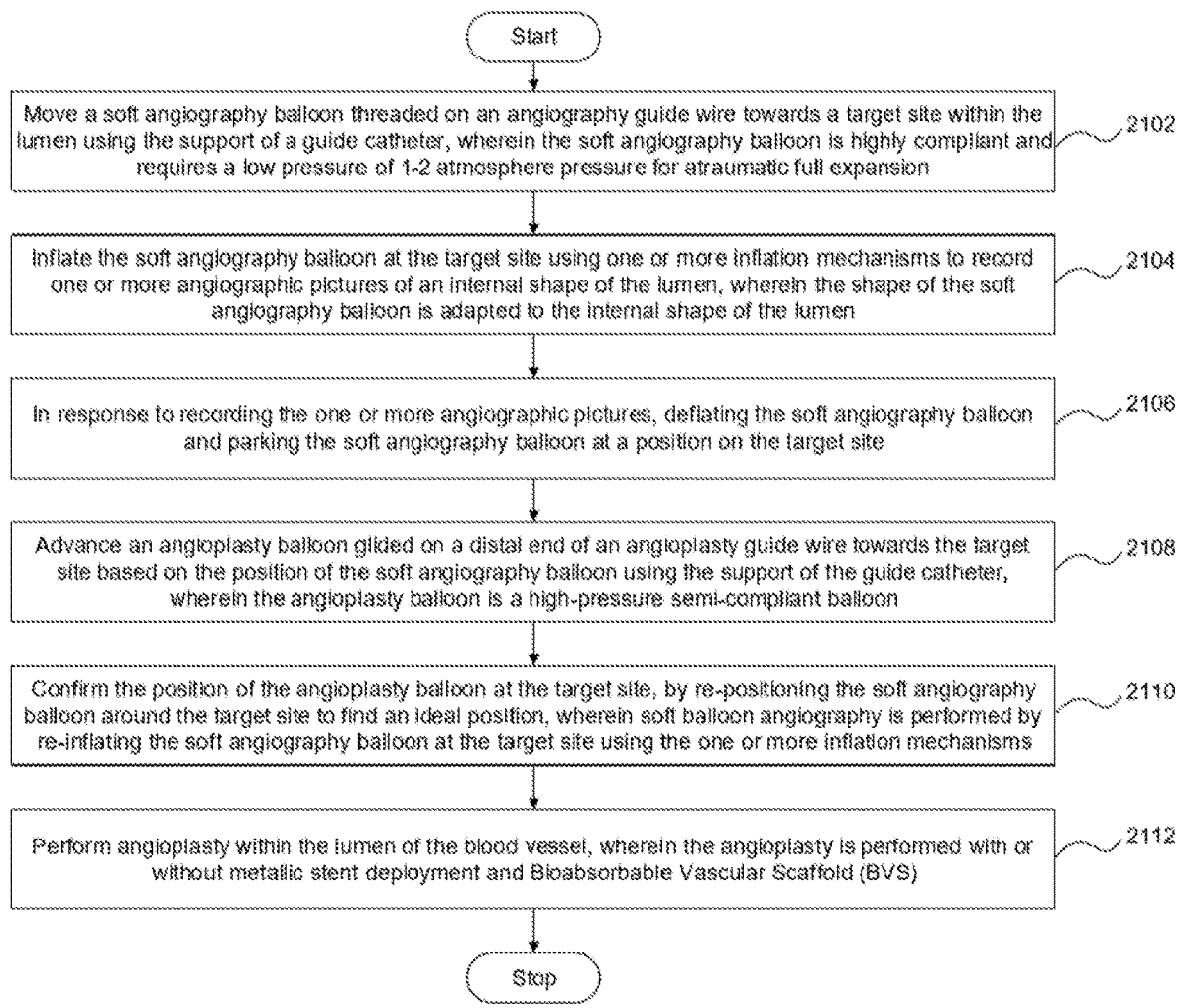
FIG. 21 illustrates flowchart of a method for performing angiography and angioplasty within the lumen of a blood vessel in accordance with an embodiment of the invention.

FIG. 21 illustrates flowchart of a method for performing angiography and angioplasty within lumen of blood vessel 102 in accordance with an embodiment of the invention.

At step 2102, soft angiography balloon 108 threaded on angiography guide wire 106 is moved towards target site 122 within the lumen of blood vessel 102 using the support of guide catheter 104, wherein soft angiography balloon 108 is highly compliant and requires a low pressure of 1-2 atmosphere pressure for full expansion. Target site 122 within the lumen of blood vessel 102 may include, but need not be limited to, one or more atheromatous plaques, one or more swellings, one or more stenoses, one or more unexpanded metallic stents and/or a Bio-absorbable Vascular Scaffold (BVS).

Upon reaching soft angiography balloon 108 at target site 122, at step 2104, soft angiography balloon 108 is inflated using the one or more inflation mechanisms to record one or more angiographic pictures of an internal shape of the lumen and the shape of soft angiography balloon 108 is adapted to the internal shape of the lumen.

The one or more inflation mechanisms may include, but need not be limited to, injecting contrast agent 132 into soft angiography balloon 108 to inflate soft angiography balloon 108 in the lumen at target site 122 to record one or more angiographic pictures of the internal shape of the lumen at the position. Also, contrast agent 132 injected into soft angiography balloon 108 may include, but need not be limited to, iodinated agents, high osmolar ionic agents, low osmolar non-ionic, iso-osmolar agents and barium-based agents and prevents excretion of contrast agent 132 through the kidneys which results in impaired renal function.

In response to recording the one or more angiographic pictures, at step 2106, soft angiography balloon 108 is deflated and is parked at a position in target site 122. Further, the deflated soft angiography balloon 108 is advanced towards a second position at distal target site 124 guided by one or more markers proximal 111 and distal 113 after re-inflating soft angiography balloon 109 to record two or more angiographic pictures of the internal shape of the lumen at the second position.

Further, the one or more angiographic pictures recorded at the position in target site 122 and the second position at distal target site 124 are stitched together into a single image for analysis using the one or more markers proximal marker 110 and distal marker 113. The two or more angiographic pictures are stitched sequentially, arranged and superimposed.

In an ensuing step 2108, angioplasty balloon 130 glided on the distal end of angioplasty guide wire 128 is advanced towards target site 126 based on the position of soft angiography balloon 108 using the support of guide catheter 104, where in angioplasty balloon 130 is the high-pressure semi-compliant balloon.

Once angioplasty balloon 130 reaches target site 126, at step 2110, the position of angioplasty balloon 130 is confirmed at target site 126 by re-positioning soft angiography balloon 108 around target site 126 to find an ideal position and re-inflating soft angiography balloon 108 at target site 126 using the one or more inflation mechanisms.

Upon confirming the position of angioplasty balloon 130, by using soft angiography balloon 108 at step 2112, angioplasty or POBA (Plain Old Balloon Angioplasty) is performed within the lumen of blood vessel 102, in conjunction with or with pre-mounted metallic stent 136 on the high-pressure semi-compliant angioplasty balloon 134 or Bioabsorbable Vascular Scaffold (BVS) deployment. Further, angioplasty is performed by expanding pre-mounted metallic stent 136 upon inflating semi-compliant angioplasty balloon 134 using the one or more inflation mechanisms. Upon expanding angioplasty stent balloon 134, pre-mounted metallic stent 136 or BVS are left at target site 126. By deflating angioplasty stent balloon 134 along with angioplasty guide wire 128 are withdrawn from the human body. Final angiogram is done by re-advancing soft Angiography balloon 108 across the target and re-inflating at low pressure and procedure is completed by withdrawing both balloon and wire out of body.

The invention utilizes an apparatus to perform angiography using a soft angiography balloon glided over an angiography guide wire, up to the target site inserted into the lumen of the blood vessel. The contrast agent is injected inside the lumen of soft angiography balloon without allowing the contrast agent to come in direct contact with one or more of blood vessels or tissues of the lumen. Thus, the side effects associated with the usage of large volume of contrast agent and its excretion through kidneys leading to Contrast Induced Nephropathy (CIN) and Acute Renal Failure, Left Ventricular failure are avoided.

Further, the soft angiography balloon is used as an assistive technology to obtain one or more angiographic pictures while performing Plain Old Balloon Angioplasty (POBA).

Also, the soft angiography balloon parked at a position in the target site is used to confirm the position of an angioplasty balloon or for deploying the pre-mounted metallic stent or Bioabsorbable Vascular Scaffold (BVS) at the target site or multiple sites.

Moreover, the invention utilizes an apparatus and method of performing angiography for defining anatomy of vessels, diameter and length of blood vessels, diagnosing vascular narrowing or dilations in the blood vessels and other hollow tubular structures without allowing the contrast agent to come in direct contact with the blood vessels or tissues of the lumen.

Further, the apparatus confirms the adequacy of expansion of the metallic stent or BVS placed at the target site inside the lumen of the blood vessel for avoiding improper deployment like under expansion.

The soft angiography balloon is developed to confirm the severity of the vascular anomalies, narrowings, dilatations, positioning of angioplasty balloon or stent accurately during the diagnostic angiography and therapeutic Percutaneous Coronary Intervention (PCI). Also, the soft angiography balloon is used in assessing the success of PCI, that is, adequacy and inadequacies, dilatation and luminal gain.

Additionally, the soft angiography balloon is also anticipated that it could replace IVUS or OCT in evaluating full expansion of deployed devices, be it a metallic stent or BVS and beyond.

Those skilled in the art will realize that the above recognized advantages and other advantages described herein are merely exemplary and are not meant to be a complete rendering of all of the advantages of the various embodiments of the invention.

In the foregoing specification, specific embodiments of the invention have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of the invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A method for performing angiography and angioplasty within a lumen of a blood vessel, the method comprising:
    moving a soft angiography balloon threaded on an angiography guide wire towards a target site within a lumen of a blood vessel using the support of a guide catheter, wherein the soft angiography balloon is configured to fully inflate via a contrast agent disposed therein such that the soft angiography balloon conforms to an internal shape of the lumen without compressing or altering the internal shape, wherein the soft angiography balloon is configured to fully retain the contrast agent such that no contrast agent contacts an external surface of the soft angiography balloon or the blood vessel;
    inflating, with the contrast agent, the soft angiography balloon at a first position of the target site, wherein the soft angiography balloon conforms to the internal shape at the first position;
    recording, at the first position, one or more angiographic pictures of the internal shape;
    in response to recording the one or more angiographic pictures, deflating the soft angiography balloon;
    advancing the deflated soft angiography balloon towards a second position at the target site;
    re-inflating, with the contrast agent, the soft angiography balloon at the second position such that the soft angiography balloon conforms to the internal shape at the second position;
    recording two or more angiographic pictures of the internal shape at the second position;
    advancing, on an angioplasty guide wire that is independent from the angiography guide wire, an angioplasty balloon towards the target site based on the angiographic pictures recorded at at least one of the first position and the second position, wherein the angioplasty balloon comprises a high-pressure semi-compliant balloon that is entirely physically separate from the soft angiography balloon, wherein no contrast agent contacts an external surface of the angioplasty balloon;
    re-positioning the soft angiography balloon around the target site to determine an ideal position for the angioplasty balloon; and
    performing, via the angioplasty balloon, angioplasty at the ideal position.

2. The method of claim 1, wherein the target site comprises at least one of one or more atheromatous plaques, one or more swellings, one or more stenoses, one or more unexpanded metallic stents and a bioabsorbable vascular scaffold (BVS).

3. The method of claim 1, wherein inflating the soft angiography balloon with the contrast agent prevents excretion of the contrast agent through the kidneys.

4. The method of claim 1, wherein the contrast agent comprises at least one of iodinated agents, high osmolar ionic agents, low osmolar non-ionic, iso osmolar agents and barium-based agents.

5. The method of claim 1, wherein the second position at the target site is guided by one or more markers.

6. The method of claim 5, further comprising stitching together, by one or more processes, the two or more angiographic pictures of the internal shape of the lumen into a single image for analysis using the one or more markers, wherein the two or more angiographic pictures are stitched sequentially, arranged and superimposed.

7. The method of claim 1, wherein recording the angiographic pictures occurs in conjunction with performing the angioplasty.

8. The method of claim 7, further comprising assessing, before and after the angioplasty, an internal diameter of the lumen of the blood vessel.

9. The method of claim 8, further comprising deploying a metallic stent to confirm that the angioplasty was successful, wherein assessing the internal diameter of the lumen further comprises assessing the internal diameter of the lumen before and after deployment of the metallic stent.

10. The method of claim 9, further comprising deploying a bioabsorbable vascular scaffold (BVS) to confirm that the angioplasty was successful, wherein deploying the BVS comprises fully expanding Polymer L-Lactide Acid (PLLA) nonmetallic struts of the BVS without Optical Coherence Tomography (OCT), additional equipment, hardware or software.

11. The method of claim 1, further comprising using a pre-mounted metallic stent on the high-pressure semi-compliant angioplasty balloon, wherein the pre-mounted metallic stent is expanded upon inflating the high-pressure semi-compliant angioplasty balloon, wherein the expanded pre-mounted metallic stent is left at the target site by deflating the high-pressure semi-compliant angioplasty balloon.

12. The method of claim 1, wherein inflating the soft angiography balloon comprises inflating the soft angiography balloon at an atmospheric pressure in a range between one (1) atm and two (2) atm.

* * * * *